United States Patent [19]

Brunsting et al.

[11] 4,199,686

[45] Apr. 22, 1980

[54] DARK FIELD ILLUMINATOR AND COLLECTOR APPARATUS AND METHOD

[75] Inventors: Albert Brunsting, Miramar; Walter R. Hogg, Dade County, both of Fla.

[73] Assignee: Coulter Electronics, Inc., Hialeah, Fla.

[21] Appl. No.: 929,267

[22] Filed: Jul. 31, 1978

[51] Int. Cl.² .................. G01J 1/58; G01N 21/38; G01N 21/00; G01N 33/16
[52] U.S. Cl. .................. 250/459; 250/461 B; 350/91; 356/342; 356/39
[58] Field of Search .............. 250/461 R, 461 B, 504, 250/574, 458, 373, 343, 459; 356/39, 317, 318, 301, 335, 337, 338, 342; 350/91

[56] References Cited

U.S. PATENT DOCUMENTS

| | | | |
|---|---|---|---|
| 2,661,658 | 12/1953 | Dyson | 350/91 |
| 3,457,407 | 7/1969 | Goldberg | 356/338 |
| 3,622,796 | 11/1971 | Harris | 356/342 |
| 3,946,239 | 3/1976 | Salzman et al. | 356/39 |

FOREIGN PATENT DOCUMENTS 962084 2/1975 Canada ............... 356/103
1029981 4/1978 Canada ............... 356/85

OTHER PUBLICATIONS

Brochure, "Pulse Cytophotometer ICPII", Phywe Aktiengesellschaft 34 Göttingen, undated.

*Primary Examiner*—Alfred E. Smith
*Assistant Examiner*—Carolyn E. Fields
*Attorney, Agent, or Firm*—William A. Newton

[57] ABSTRACT

There is disclosed an illuminator and collector apparatus and method for fluorescence analysis wherein illumination of a stream of particles produces fluorescent light. A reflector, having a concave reflector surface with a first focus disposed in the stream of particles, has reflected therefrom organized illuminating radiation, such radiation converging upon the first focus to stimulate the particles into producing the fluorescent light. The fluorescent light emanates from the first focus, a portion of which is reflected from the concave reflector surface. This fluorescent light which is focused on the second focus contains no (or negligible) amount of illuminating radiation and is collected for subsequent detection and processing.

27 Claims, 8 Drawing Figures

DARK FIELD ILLUMINATOR AND COLLECTOR APPARATUS AND METHOD

FIELD OF THE INVENTION

The present invention relates to the illumination of individually isolated particles and the collection of resultant fluorescent light emanating from the particles being stimulated by the illumination.

DISCUSSION OF THE PRIOR ART

In the art of cytology, individual cells may be differentiated on the basis of quantitative and qualitative characteristics, one of these characteristics being the cell's staining behavior. In techniques which evaluate staining behavior, the cell constitutents (for example, DNA RNA, and protein) to be measured are tagged with fluorescent dyes which fluoresce when illuminated, while the rest of the cell remains relatively dark at the wavelength of the fluorescence. The intensity of the fluorescent light and the amount or type of cell constituent are correlated so as to provide a basis for analysis of collected data. Consequently, it is critically important that the collected fluorescent signal correspond to the amount of nonhomogeneously distributed fluorescent material contained within the cell and not be dependent upon cell's orientation and/or position in the illuminating radiation. Therefore, it may readily be seen that uniformity of illumination of the fluorescent material within a given cell is essential to obtaining accurate and reliable results.

As has recently become appreciated, illumination of cells with relatively narrow beams of illuminating radiation, such as laser light, creates "hot spots", i.e., regions of relatively large energy density as compared to neighboring regions within the cell. These "hot spots" are due to optical effects at cell and organelle boundaries. This is particularily true of cells being irradiated by collimated radiation. Moreover, it is known in the art that converging beams, e.g., laser radiation, with a Gaussian intensity profile, become collimated in the focal region due to diffraction and therefore create the "hot spots" in the same manner. The problem with these "hot spots" is that if they coincide in location with the regions of fluorescent material within the cell, then that fluorescent material gives off a high intensity fluorescent signal relative to a low intensity fluorescent signal that the same fluorescent material would have produced if it had not been in the "hot spot". Thus, when many identical cells are so illuminated and their fluorescence measured, an artifical broadening of their fluorescence distribution is observed due to the "hot spot" coinciding with regions of high fluorescent material in some cells and regions of low fluorescent material in other cells.

The fluorescent radiation can produce "hot spots" also as it emerges from the particle or cell in a similar manner as the illuminating radiation produces "hot spots". This is due to the structure of the refractive index (in general complex) within a cell and the cell-exterior optical boundary. Even if a non-spherical cell was illuminated so that all of its non-homogeneously distributed fluorescent material received an equal amount of radiation, still the amount of fluorescent light emerging from the cell and subsequently measured depends on cell orientation with respect to the detector means and the structure of the refractive index (in general complex) within the cell and the cell-exterior optical boundary. Consequently, a large solid angle of collection of fluorescence is needed in addition to a large solid angle of illumination when analysing particles, or more particularily, biological cells.

It has also been found desirable in the prior art devices to collect the fluorescent light from a "dark field". A "dark field" consists of a condition in which the fluorescent light reaching the fluorescence detector is relatively free of the illuminating radiation. If the illuminating radiation is of a substantial intensity in comparison to the fluorescent light as viewed by the fluorescence detector, then the measurement of fluorescent light is made difficult (or impossible in some cases) due to the poor optical signal to noise ratio (meaningful optical rays compared to unwanted rays). Consequently, there developed in the prior art the concept of collecting the fluorescent light from a "dark field" so that the concentration of intermingled illuminating radiation would be minimized in the presence of the fluorescent light and the optical signal to noise ratio would be maximized.

A cytophometer of the prior art which incorporates the "dark field" concept is sold under the trademark "Phywe". The Phywe device irradiates the particles with radiation made to converge to a focus by a lens so as to intersect with the particles at the focus. The radiation diverges past the particles after having converged to the focus. The converging radiation proceeds through an orifice, such orifice also being adapted to receive fluorescent light which travels along the same path as the illuminating radiation but in the reverse direction, to be collected by the above mentioned lens. The orifice and the lens thereby determine both the collection of the fluorescent light and the maximum angle of the illuminating radiation (i.e., numerical aperture) both of which are relatively small as compared to the total solid angle of $4\pi$ steradians.

The inventors of the invention presented herein perceived that the way to correct the "hot spot" problem was to illuminate the particles from many different directions so as to smear out the "hot spots" altogether. Moreover, the inventors desired to increase the fluorescent light collection from a "dark field" over that found in the prior art devices, while illuminating the particles in as many different directions as possible.

SUMMARY OF THE INVENTION

The present invention is directed toward an illuminator and collector apparatus and method for fluorescence analysis wherein illumination of a stream of particles stimulates detectable fluorescent light.

The illuminator and collector apparatus comprises a reflector having a concave reflector surface with a first focus positioned in intersecting relationship with the stream of particles. The apparatus further comprises illuminating means to provide organized illuminating radiation which reflects from the concave reflector surface and converges on the particles at the first focus to stimulate the fluorescent light. A portion of the stimulated fluorescent light reflects from the concave reflector surface and is focused on a second focus of the concave reflector surface. The apparatus further comprises radiation separating means for segregating the fluorescent light proceeding from the concave reflector surface from the illuminating radiation proceeding toward the concave reflector surface. By virtue of this arrangement, the illuminating radiation proceeds outward in a divergent manner from the first focus, while the organized fluorescent light focused on the second focus is collected for subsequent detection and processing.

The method includes the steps of illuminating the particles passing through the first focus of the concave reflector surface by reflecting organized illuminating radiation off of the concave reflector surface so that the illuminating radiation converges on the first focus. The method further includes the step of collecting for subsequent detection organized fluorescent light which has reflected from the concave reflector surface.

BRIEF DESCRIPTION OF THE DRAWINGS

Further objects and advantages of the present invention will become apparent as the following description proceeds, taken in conjunction with the accompanying drawings in which:

FIG. 8 is a generalized diagrammatic representation of the illuminator and collector apparatus of the present invention.

DETAILED DESCRIPTION OF THE PREFERRED EMBODIMENT

There is disclosed apparatus means and a method for fluorescent analysis wherein particles are illuminated from many different directions so as to produce resultant fluorescent light which is subsequently collected from preferably substantially all other directions against a dark field. When particles are illuminated by a relatively narrow beam, particle to particle variations cause a spurious spread in the fluorescence measurements which is a function of particle orientation and position and the distribution of the fluorescent materials within the particle and not a function of the amount of fluorescent material within the particle. Consequently, the present invention contemplates providing apparatus means and a method for minimizing the spurious effects of particle-to-particle variations and at the same time collecting substantially all of the resultant fluorescent light available against a dark field.

Figure 1:
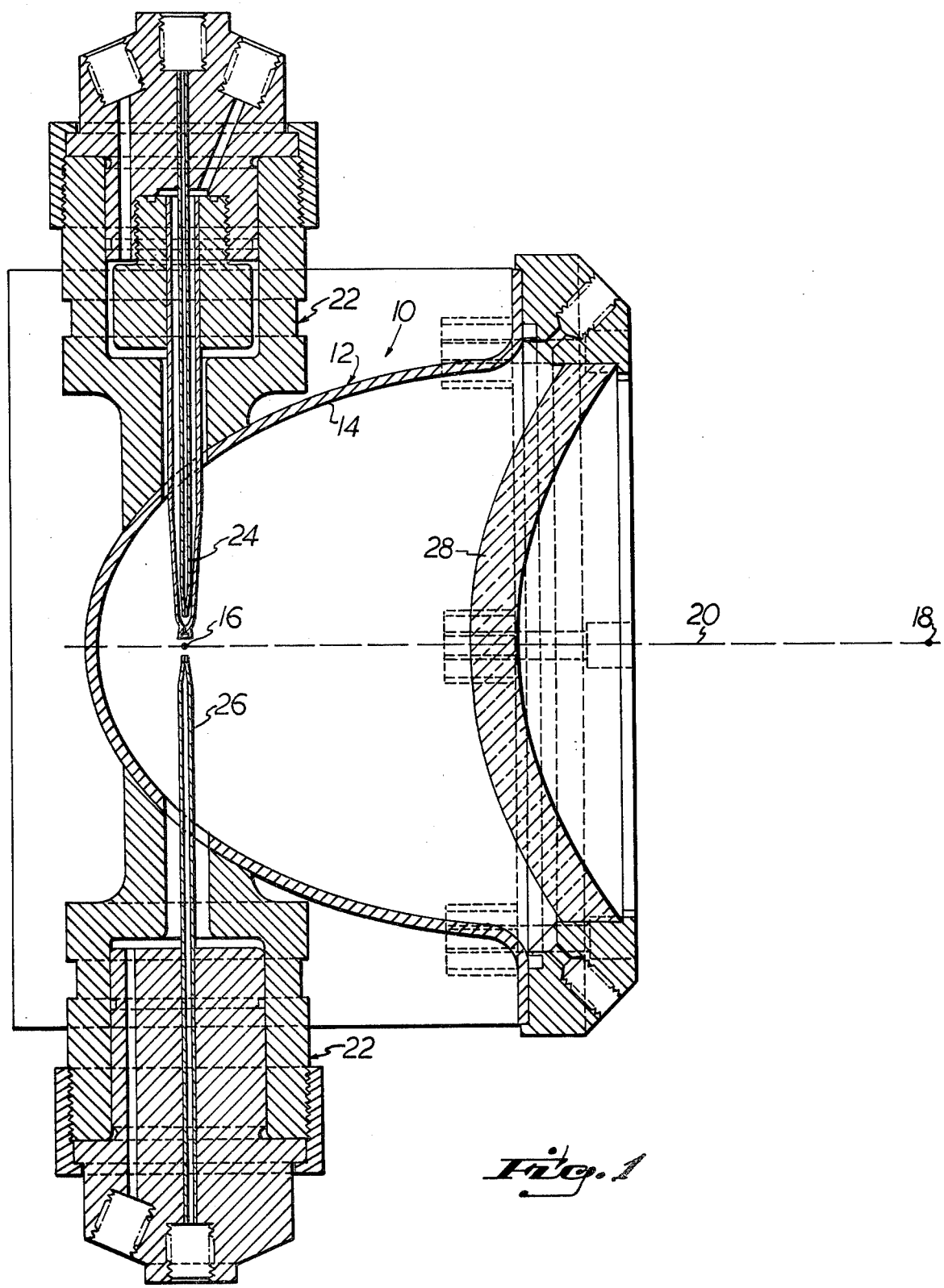
FIG. 1 shows a cross section of a first embodiment of an illuminator and collector apparatus having an ellipsoidal concave reflector surface.

There is illustrated in FIG. 1 a first embodiment of an illuminator and collector apparatus, generally identified by numeral 10. In this embodiment, the apparatus 10 comprises a reflector 12 having a concave reflector surface 14. The concave reflector surface 14 has the configuration of a portion of an ellipsoid (ellipse rotated about its major axis). The concave reflector surface 14 has a first focus 16 and a second focus 18 disposed on an optical axis 20. The apparatus 10 has a particle source (not shown) which provides particles to a particle entraining structure 22 having an entrance tube 24. The particles are entrained in a stream of individually isolated particles from the entrance tube 24 through the first focus 16 and into an exit tube 26 so as to be directed to a particle exit (not shown). This flow of particles is normally suspended in a fluid, either gas or liquid. A window 28 is provided for confining the fluid, such window 28 being optional in the case of usage of a gas. The window 28 also provides the entrance for the illuminating radiation and an exit for the resultant fluorescent light. The preferably spherical window 28 has its center located at the second focus 18 so as to provide for a minimum of optical perturbation. It should be understood that providing a stream of individually isolated particles with a chamber filled with a fluid is accomplished in a manner and by means well known in the art.

Figure 2:
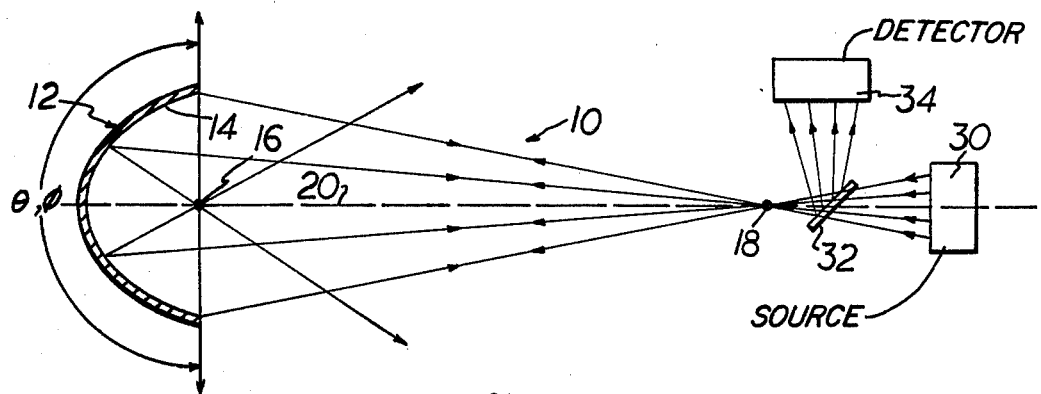
FIG. 2 shows a schematic cross sectional diagram of the first embodiment of the illuminator and collector apparatus having the ellipsoidal concave reflector surface subtending a $2\pi$ steradian solid angle.

The actual operation of the first embodiment of apparatus 10 is better understood by referring to the schematic of FIG. 2. A source 30 of illuminating radiation provides illuminating radiation which is convergent upon and passes through the second focus 18 so as to impinge upon the concave reflector surface 14. By virtue of the well known geometrical properties of an ellispoid of revolution, a ray proceeding from one focus 16 or 18 so as to impinge upon the concave reflector surface 14 is reflected toward the other focus 16 or 18. Consequently, the illuminating radiation after one reflection converges upon the first focus 16 so as to illuminate the particles passing therethrough. The particles are illuminated from many different directions over an illumination solid angle $\theta$. In this manner, effects of the "hot spots" in illumination previously described in the Prior Art section are reduced, resulting in a closer correlation between the collected fluorescent light and the amount of fluorescent material contained within a cell. Once the particles are illuminated, most of the illuminating radiation proceeds through the first focus 16 and diverges. It is important to note that in FIG. 2 this diverging illuminating radiation is not reflected a second time by the concave reflector surface 14. If such illuminating radiation had been reflected a second time by the concave reflector surface 14, then it would have been reflected so as to converge on the second focus 18. The illumination of the flluorescent dye attached to the stained cells produces fluorescent light which radiates (generally, but not perfectly) isotropically from the first focus 16. A portion of this fluorescent light, within the collection solid angle $\phi$, is reflected from the concave reflector surface 14 and thereby converges toward the second focus 18. In that the fluorescent light may be collected over a relatively large collection angle $\phi$, effects of "hot spots" in collection described in the Prior Art section are reduced.

By virtue of the relationship between the diverging illuminating radiation proceeding from the first focus 16 and the flluorescent radiation converging upon the second focus 18, as illustrated in FIG. 2, the fluorescent light converging upon the second focus 18 may be collected with a negligible amount of illuminating radiation within the collection solid angle φ. More specifically, in FIG. 2, the illuminating radiation proceeding from the first focus 16 is contained within θ where here θ=2π steradians. Therefore, the concentration of illuminating radiation which is commingled with the flluorescent light is greatly reduced relative to a situation in which the two beams are coincident. Since φ is exclusive of θ, the fluorescent light may be described as being collected from a relatively dark field. This means that there is a greatly improved optical signal (fluorescent light) to noise (illuminating radiation) ratio.

As illustrated in FIG. 2 the apparatus 10 includes means for splitting away the incoming illuminating radiation proceeding toward the second reflector surface 14 from the outgoing fluorescent light. The radiation separating means may take the form of numerous conventional means well known in the art, such as a prism, or as shown in the preferred embodiments, a dichroic reflector 32 which reflects only that light below or above a given cutoff wavelength. As a secondary function, the dichroic reflector 32 may be used to assist in filtering out illuminating radiation which has been intermingled with the fluorescent light due, for example, to overlapping θ+φ or to scattering. (There may be other sources not mentioned here). Although the dichroic reflector 32 is positioned past the second focus 18 relative the concave reflector surface 14, it could have been positioned before the second focus 18. Although the dichroic reflector 32 is shown reflecting illuminating radiation, while passing through fluorescent light, the dichroic reflector 32 could be designed to pass illuminating radiation and reflect fluorescent light. In either case the fluorescent radiation is directed toward an optical detector 34. The optical detector 34 shown in FIG. 2 is of a conventional design and converts detectable fluorescent light to electrical signals so as to provide for subsequent data acquisition. The typical detector 34 would comprise well known photosensitive detectors, preferably in the form of photomultipler tubes, vacuum photodiodes or solid state photodiodes. The optical detector 34 may optionally include a conventional color barrier filter.

As explained heretofore, the illuminating radiation diverges from the first focus 16 relative to the fluorescent light convergent on the second focus 18. Consequently, the fluorescent light proceeding toward the second focus 18 may be collected with an improved signal to noise ratio. Even with this divergent relationship a miniscule center cone of illuminating radiation centered on the optical axis 20 proceeds directly from the first focus 16 and impinges on the dichroic reflector 32, therefore representing undesirable noise. Although such noise may be tolerable, the following paragraphs will discuss some of the adjustments that may be made to eliminate or minimize this cone of illuminating radiation.

Figure 3:
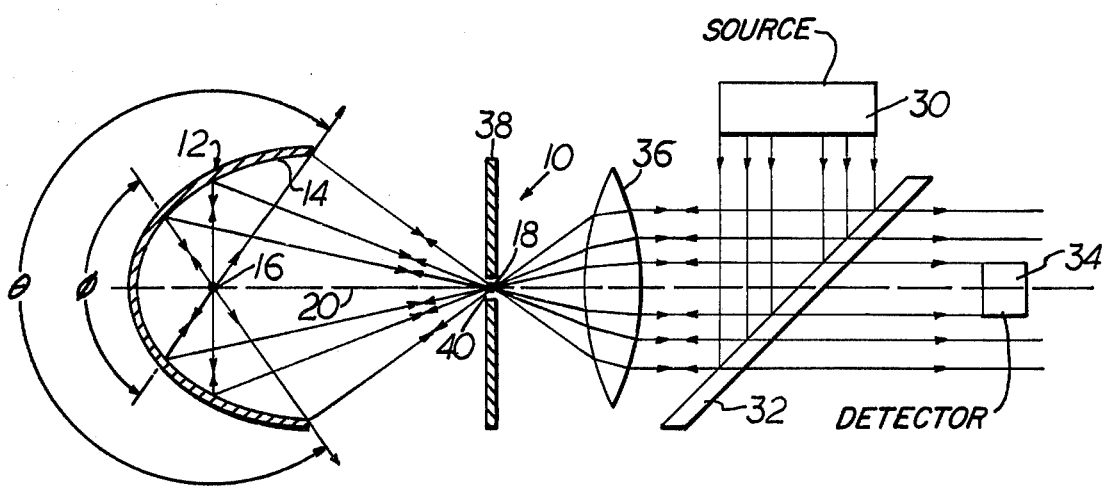
FIG. 3 shows a schematic cross sectional diagram of the first embodiment of the illuminator and collector apparatus having an extended ellipsoidal concave reflector surface and a larger illumination angle relative to those of FIG. 2.

Referring to FIG. 2, as one's point of reference is moved along the optical axis 20 from the focus 16 to the focus 18 of FIG. 2 the intensity of the illuminating radiation from 16 is decreased in proportion to the inverse square of the distance moved. On the other hand, as the point of reference is so moved along the optical axis 20, the fluorescent light converges toward the second focus 18. Consequently, collection of the fluorescent light in the proximity of the second focus 18 would reduce the amount of illuminating radiation reaching the detector 34. Also, as the eccentricity of the concave reflector surface 14 is increased, the second focus 18 is pushed outward with the effect of further minimizing the solid angle subtended by the dichroic reflector 32 and hence the amount of illuminating radiation commingled with the fluorescent light in the vicinity of the second focus 18. The above explanation of ellipsoidal eccentricities is provided merely to illustrate the physical characteristics and relationships inherent in the apparatus 10. It should be appreciated that the amount of illuminating radiation commingled with the fluorescent light at the point of collection may be minimized by decreasing the size of the dichroic reflector 32 of FIG. 2 by moving the reflector 32 closer to the second focus 18 and/or by moving the dichroic reflector 32 and the second focus 18 outward by increasing the eccentricity of the ellipsoid. However, there are practical limitations on the eccentricity of the ellipsoid and smallness of the dichroic reflector 32. Additional means may be included which eliminate the need for such above described design difficulties. For instance, as illustrated in FIG. 3, such means may include an opaque barrier 38 having a pinhole aperture 40 formed therein. It should be appreciated that the solid angle subtended by the aperture 40 as viewed from the focus 16 is a very small fraction of θ. Also, the inclusion of one or more lenses may divert substantial portions of this cone of illuminating radiation. With the inclusion of such means, the cone of stray illuminating radiation centered on optical axis 20 which might normally be collected by the optical detector 34 is effectively eliminated.

A variation of the first embodiment is illustrated in FIG. 3 in which collimated light proceeds from the source 30 to the lens 36. The achromatic lens 36 (used for both illuminating and fluorescent light) subsequently converges the illuminating radiation toward the second focus 18, whereby the illuminating radiation proceeds through the second focus 18 and impinges on the reflector surface 14. As with all lenses utilized in combination with the present invention, a reflector might be used in its place. Moreover, it should be appreciated that there is no intent to limit the present invention to be any specific lens or reflector arrangement or any combinations thereof in that such arrangements may take many different forms which are well known to those skilled in the art. Consequently, the means disclosed for manipulating the reflected fluorescent light and for focusing the illuminating radiation are intended to be merely illustrative.

For the purposes of illustration, in FIG. 2 the reflector surface 14 is shown subtending a 2π steradian solid angle at the first focus 16 with the illuminating radiation irradiating the entire reflector surface 14. By virtue of this design, particles passing through the first focus 16 are illuminated over a 2π steradian solid angle. It is important to note that with this design the illuminating radiation, after passing through the first focus 16, does not undergo any further reflection off of the reflector surface 14. This is significant in that further reflection of the illumination radiation would cause the illuminating radiation to converge on the second focus 18. The consequence of this is that it would become commingled with the collected fluorescent light and/or cause unwanted stray light. In the embodiment shown in FIG. 2, the illumination angle θ of 2] steradians represents the maximum illumination that can be obtained without the illuminating radiation reflecting from the concave reflector surface 14 for a second time. In actual practice, the illumination of the particles in this embodiment would be slightly less than $2\pi$ steradians due to the solid angles subtended by such items as entrance and exit tubes 24 and 26.

In FIG. 3 the concave reflector surface 14 is extended so as to form more than a $2\pi$ steradian solid angle at the first focus 16. The incident illuminating radiation is correspondingly expanded to preferably impinge upon the entire concave reflector surface 14. When the illuminating angle $\theta$ exceeds $2\pi$ steradians, the portion of the illuminating radiation which is reflected twice from the concave reflector surface 14 converges toward the second focus 18 with the fluorescent light. If one is to examine a cross sectional view of the fluorescent light focused on the second focus 18, it should be noted that the commingling of the illuminating radiation with the fluorescent light begins at the periphery of the cross sectional view of the fluorescent light and extends inward toward the center to an increasing extent as the illumination angle $\theta$ is increased over $2\pi$ steradians. Consequently, by collecting only predetermined center portions of the fluorescent light focused on the second focus 18, the perpherial portions having commingled illuminating radiation may be avoided. This allows the illuminating angle $\theta$ to exceed $2\pi$ steradians without collecting the resultant commingled illuminating radiation caused by the illumination angle exceeding $2\pi$ steradians. There are numerous ways in which one skilled in the art could collect the above described center portion of fluorescent light which is relatively free of commingled illuminating radiation. For instance, the optical detector 34 could be cooperatively configured and dimensioned to selectively receive the fluorescent light as shown in FIG. 3. Alternatively, an aperture of predetermined dimensions may be interposed before the fluorescent light reaches the optical detector 34 to pass only the desired fluorescent light or the dichroic reflector 32 may be configured and dimensioned to reflect only the desired fluorescent light, or similar such means obvious to one skilled in the art.

Figure 4:
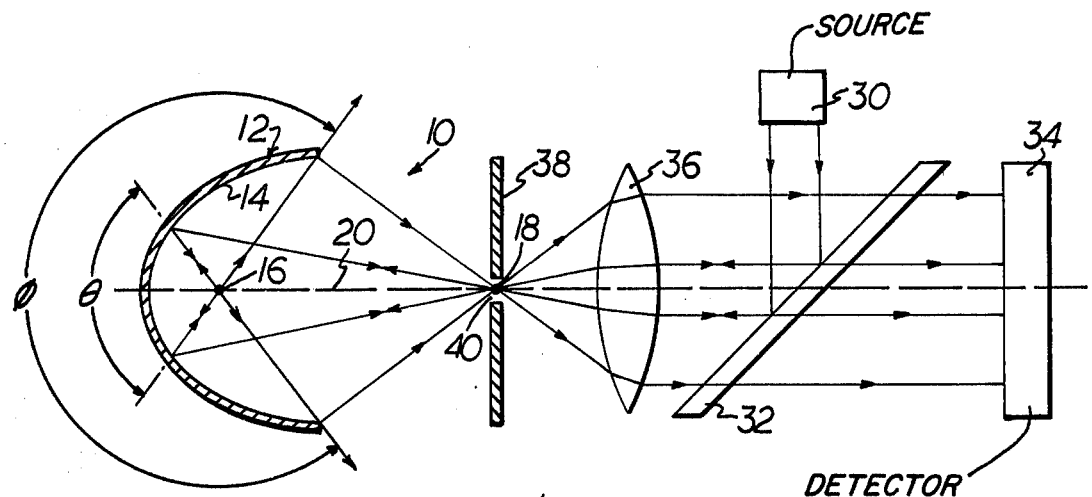
FIG. 4 shows a schematic cross sectional diagram of the first embodiment of the illuminator and collector apparatus having an extended ellipsoidal concave reflector surface and a larger fluorescent collection angle relative to those of FIG. 2.

In FIG. 4 the concave reflector surface 14, as in FIG. 3, is extended to define a solid angle formed at the first focus 16 which is greater than the $2\pi$ steradian solid angle. In this embodiment the illumination angle $\theta$ is decreased with a corresponding increase in the fluorescent collection angle $\phi$. It should be noted that the fluorescent collection angle $\phi$ represents that amount of fluorescent light which may be collected without the illuminating radiation overlapping so as to be reflected twice from the concave reflector surface 14 and converge toward the second focus 18. In other words, it does not necessarily represent all of the fluorescent light that is being reflected from the concave reflector surface 14. The specification of the illuminating radiation to impinge upon the preselected area of the concave reflector surface 14 may be accomplished by numerous means obvious to one skilled in the art, such as providing the source 30 of predetermined configuration and dimensions, such as in FIG. 4, or by using a confining aperture interposed to limit the illuminating radiation prior to impinging upon the concave reflector surface 14, or by having a dichroic reflector 32 which is of a predetermined limited size, or by similar equivalent means.

As is illustrated in FIGS. 3 and 4, it may be desirable, depending on the type of cells or particle being studied, to decrease or increase the illumination angle $\theta$ with respect to the $2\pi$ steradian value illustrated in FIG. 2 with an equal increase or decrease, respectively, in the fluorescent collection angle $\phi$. The following relationship exists between the collection and illumination with a maximum amount of fluorescent light collected from a relatively dark field:

$$\theta + \phi = 4\pi \text{ steradians for } 0 < \theta < 4\pi.$$

This presupposes that the concave reflector surface 14 is expanded when necessary to reflect sufficient fluorescent light or to reflect sufficient incident illuminating radiation as dictated by the above stated relationship. However, it should be appreciated that some amount of overlapping may be tolerable (viz., $\theta + \phi > 4\pi$ steradians) and in some applications it may be desirable to have gaps between the illumination and collection angles (viz., $\theta + \phi < 4\pi$ steradians).

Figure 5:
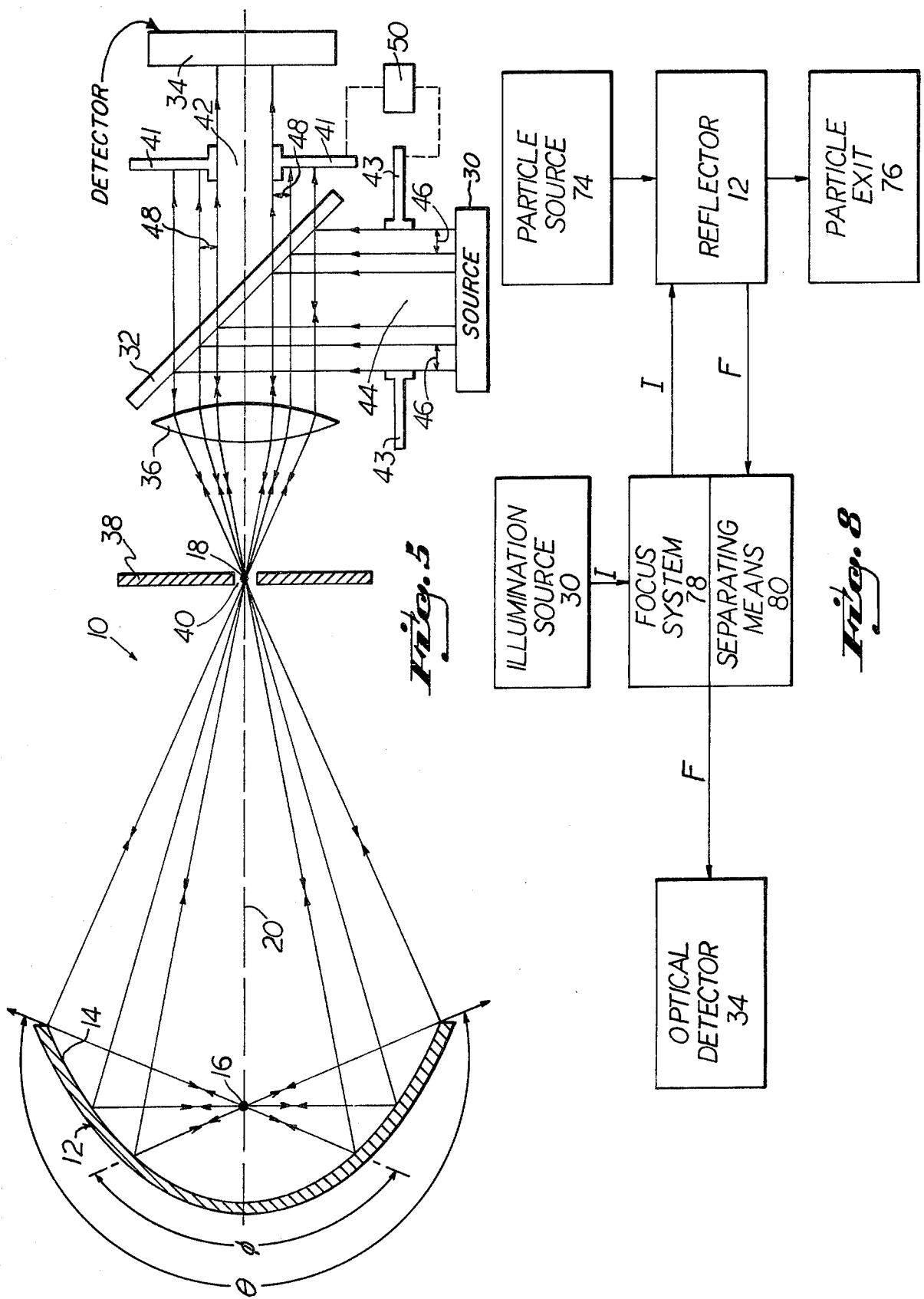
FIG. 5 shows a schematic cross sectional diagram of the first embodiment of the illuminator and collector apparatus with a pair of opaque barriers incorporated therein.

The relationship between the illumination angle $\theta$ and fluorescent collection angle $\phi$ in FIGS. 2, 3, and 4 is in part determined by the degree of the extension of the concave reflector surface 14. In the variation of the first embodiment illustrated in FIG. 5, the concave reflector surface 14 may extend past the extremities of fluroscent collection angle $\phi$ and the illumination angle $\theta$ without affecting the interrelationship between the two. In the modification of FIG. 5, a first opaque barrier 41 having a first orifice 42 and a second opaque barrier 43 having a second orifice 44 are incorporated to regulate the diameters of the collected fluorescent light and the illuminating radiation, respectively. As illustrated in FIG. 5, a diameter increase 46 of the illuminating radiation beam results in a corresponding diameter decrease 48 in the available fluorescent light collection not having illuminating radiation commingled therewith. In FIG. 5 the diameter increase 46 is an increase in excess of the beam diameter at which the illuminating angle $\theta$ is $2\pi$ steradians. It has been discovered by the inventors that the diameter increase 46 creates a solid angle increase in illumination which is equal to the solid angle decrease in fluorescence collection caused by the diameter decrease 48 and vice versa. Moreover, as previously explained, this tradeoff relationship holds true over the entire range of combinations of collection angles $\phi$ and illuminating angles $\theta$ which add up to $4\pi$ steradians with the maximum collection of fluorescent light without overlapping from a dark field. Inherent in this arrangement is the ability to adjust the tradeoff between the two angles for different types of particles and different types of tests. For instance, interchangeable pairs of first and second opaque barriers 41 and 43 respectively may be utilized to adjust the collection and illumination angles. Such pairs of barriers 41 and 43 would be configured, dimensioned and aligned to conform the illuminating radiation and the reflected fluorescent light to the previously described tradeoff relationship. Alternatively, the opaque barriers 41 and 43 may be provided with orifices 42 and 44 respectively, for example iris diaphragms, having continuously variable diameters. More specifically, the diameter of each orifice 42 and 44 could be individually adjusted to the desired value. Alternatively, the adjustment of the two diameters could be ganged by conventional regulating means, illustrated by numeral 50 to maintain automatically the desired tradeoff relationship.

Figure 6:
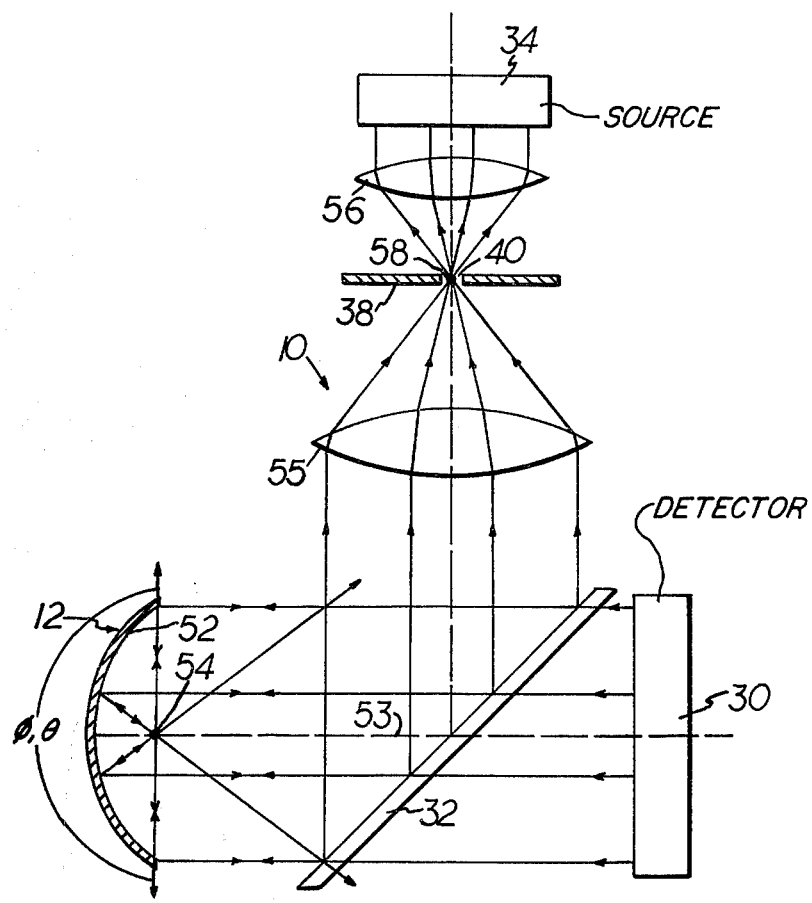
FIG. 6 shows a schematic cross sectional diagram of a second embodiment of the illuminator and collector apparatus having a paraboloidal concave reflector surface.

A second embodiment of the collector apparatus 10 is illustrated in FIG. 6. In the second embodiment elements similar to those of the first embodiment are identified by the same reference numerals. In this embodiment the reflector 12 has a paraboloidal concave reflector surface 52 with a configuration of a portion of a paraboloid of revolution. Collimated light centered on an optical axis 53 is provided by the source 30 of illuminating radiation for reflection off of the reflector surface 52, thereby resulting in convergent radiation focused on a first focus 54. For this embodiment, the apparatus 10 ideally includes a pair of lenses 55 and 56, although reflectors could be used instead of the lenses. In this embodiment a second focus (not shown) of the concave reflector surface 52 is at infinity. This leads to the reflected fluorescent light being collimated as the same proceeds from the concave reflector surface 52. Therefore, the lenses 54 and 56 are ideally, but not necessarily, incorporated to converge the fluorescent light to a third focus 58. This preferably, but not necessarily, allows for the positioning of the opaque barrier 38 with the pinhole aperture 40 at the third focus 58. Moreover, the placement of at least one lens along the path of the fluorescent light eliminates illuminating radiation which would normally radiate from the first focus 54 and impinge upon the dichroic reflector 32. In this embodiment the dichroic reflector 32 ideally, but not necessarily, is positioned before the lenses 54 and 56 so that such lenses need not be achromatic lenses. It should be understood that the present invention is not intended to be limited to any specific lens or reflector arrangement or any combination thereof for manipulating the reflected fluorescent light or for focusing the illuminating radiation in that such arrangements may take many different forms known to those skilled in the art. As with the first embodiment, the illumination angle $\theta$ and the fluorescent collection angle $\phi$ are both shown to be equal to $2\pi$. However, just as with the first embodiment, the illumination angle $\theta$ may be decreased or increased with a corresponding increase or decrease, respectively, in the fluorescent collection angle $\phi$, assuming that the concave reflector surface 52 is extended. Also, some overlapping of the illumination and the fluorescent collection or the formation of gaps are within the scope of the present invention. Moreover, the opaque barriers 41 and 43 having orifices 42 and 44 respectively, as shown in FIG. 5, may optionally be included in this embodiment.

Figure 7:
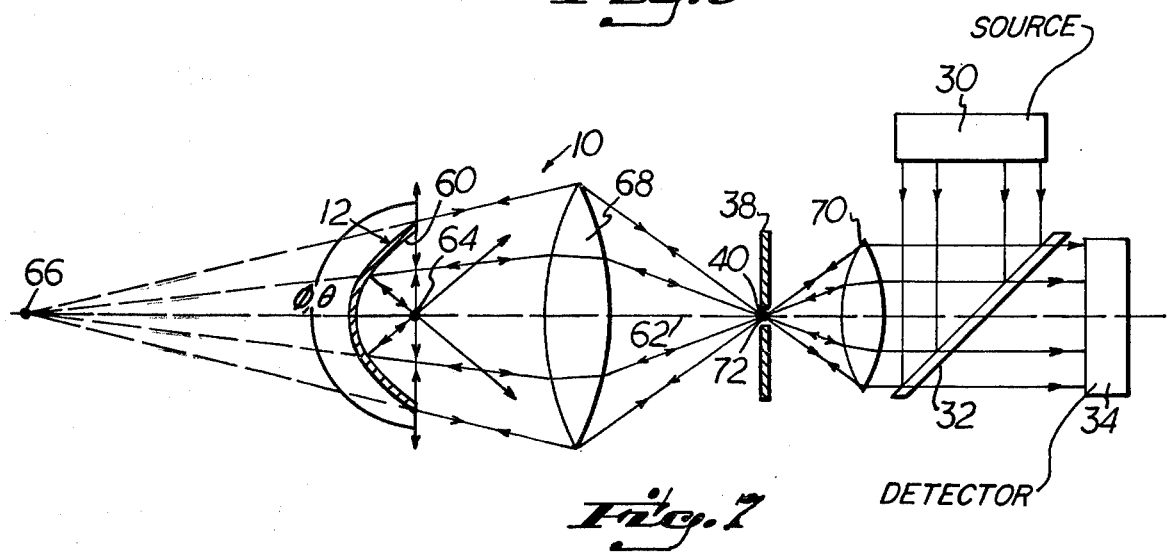
FIG. 7 shows a schematic cross sectional diagram of a third embodiment of the illuminator and collector apparatus having a hyperboloidal concave reflector surface.

A third embodiment of the apparatus 10 is shown in FIG. 7. For the third embodiment elements similar to those of the first and second embodiments are identified by the same names and reference numerals. In this embodiment the reflector 12 includes a hyperboloidal concave reflector surface 60 having the configuration of a portion of a hyperboloid of revolution. Consequently, convergent illuminating radiation is provided about an optical axis 62 which reflects from the concave reflector surface 60 and subsequently converges on a first focus 64. A second focus 66 of the concave reflector surface 60 is a virtual focus and therefore the reflected fluorescent light proceeds from the concave reflector surface 60 in a divergent manner. The illustrative lens arrangement of FIG. 7 includes lenses 68 and 70. These lenses 68 and 70 have the dual purposes of taking collimated illuminating radiation from the source 30 of illumination and then forming it into the convergent illuminating radiation to the focus 66 and at the same time providing for a third focus 72. As previously described in the discussion of the other embodiments, this type of lens arrangement allows for the fluorescent light to be converged to the third focus 72 so as to be filtered by the pinhole aperture 40 formed in the opaque barrier 38. Also, for the purpose of collecting fluorescent light, the lenses provide a secondary benefit in that the illuminating radiation whih proceeds past the first focus 64 does not pass through the aperture 40; thereby eliminating stray illuminating radiation that otherwise might have been incident on the dichroic reflector 32. As with the other embodiments, the present invention as incorporated in this embodiment may be used with other lens or equivalent reflector arrangements which would be obvious to one skilled in the art. As with the other two embodiments, the drawing shows this embodiment as having an illuminating angle $\theta$ of $2\pi$ steradians and an equal fluorescent collection angle $\phi$ of $2\pi$ steradians. Also, as with all of the embodiments, the concave reflector surface 60 may be extended so that the illumination angle may be increased or decreased with a corresponding decrease or increase, respectively, in the fluorescent collection angle. Also, some overlapping of the illumination and the fluorescent collection or the formation of gaps are within the scope of the present invention. Likewise, the opaque barriers 41 and 43 having orifices 42 and 44 respectively, as shown in FIG. 5, may optionally be included in this embodiment.

Referring to the drawings in general, the figures represent three-dimensional apparatus by sections representing the intersections of the apparatus 10 with some plane passing through the optical axis 20, 53 or 62. It may be inferred from this that the apparatus 10 is rotationally symmetrical. This may not be the case in general. In fact, the angles $\theta$ and $\phi$, as they appear in two dimensions in the figures, may be made functions of an angle between the plane of the figures and some reference position looking along the optical axis, such that their sum, as this third angle is swept from zero degrees to 360 degrees, is constant. Of course, the solid angles swept out by $\theta$ and $\phi$ as this third angle is swept through 360 degrees are the solid angles heretofore referred to. Tlhe optical apertures 42 and 44 hence may be other than circular and may be, for example, elliptical or rectangular (looking along the optical axis) to produce and conform to the desired function of $\theta$ with respect to, say, the third angle. The apparatus will perform as described as long as any section, including the optical axis, appears as one of the figures.

For the purposes of summarizing the radiation illuminator and collector apparatus 10 in a generic fashion, the apparatus 10 is broadly represented in function and structure in a schematic block diagram of FIG. 8. The apparatus 10 comprises the reflector 12 having a concave reflector surface heretofor described as being one of several possible conic sections of revolution or their equivalents with the first focus and the second focus. As illustrated in FIG. 8, a particle source 74 provides a stream of particles which are illuminated by illuminating radiation (identified as I) at the first focus, such particles subsequently passing on to the particle exit 76. Illuminating means provides and directs organized illuminating radiation toward the reflector 12. Depending upon the embodiment described heretofore, the illuminating means is adapted to provide the corresponding radiation, either convergent, divergent, or collimated, which converges at the first focus after reflecting off of the reflector 12. The type of organization clearly depends upon the type of reflector 12 that is used in that the combination of the two produces radiation which is convergent on the first focus. By virtue of this convergent radiation, the stream of particles is illuminated at the first focus to produce the resultant fluorescent radiation, including light, (identified as F) which radiates outward from the first focus. Although the stimulated fluorescent signal has been described herein as "fluorescent light", the fluorescent signal may take the form of other types of radiant energy or radiation. The illuminating means comprises the source 30 of illumination which proceeds through a focus system 78, such focus system 78 providing the organized radiation directed toward the reflector 12 positioned on the optical axis of the reflector 12. The focus system 78 includes conventional lens or reflector arrangements previously described which may take numerous forms known to the art. The source 30 of illumination may provide conventional forms of coherent and incoherent radiation used to irradiate particles, such as lasers or a high pressure mercury lamp and may include color filters. The illuminating radiation diverges past the first focus, while the resultant fluorescent light reflects from the reflector 12 and is focused on the second focus, either real as in the first and second embodiments, or virtual as in the third embodiment. This fluorescent light proceeding from the reflector 12 is split from the illuminating radiation proceeding toward the reflector 12 by radiation separating means 80, thereby allowing the fluorescent light to be collected by the optical detector 34. The focus system 78 may optionally include means for preventing that part of the diverging illuminating radiation which proceeds toward the optical detector 34 from reaching the same. The separating means 80 may reflect or divert the fluorescent light and pass the illuminating radiation or vice versa, and is therefore shown differently in different drawings merely for the purposes of illustration.

In the practical application of the radiation collector 10, the foci described herein, such as 16 and 18, are actually focal zones and not theoretical points. In the preferred embodiments the intersection of the particulate material, which may be the width of several particles, with the illuminating radiation may create a "sensing zone" of radiation at the first focus 16 having a volume of typically 10,000 cubic micrometers in the preferred embodiments. More specifically, the finite dimensions and somewhat diffused (e.g., Gaussian) distribution of radiation, convolved with the path of the particulate suspension, gives rise to this "sensing zone". This zone at the first focus is centered around a mathematical, infinitesimally small focal point and is represented in the drawings as a single point. As is well known in the art, a zone centered at the first focal point of, for example, an ellipsoid, creates a corresponding zone of radiation centered at the second focal point of the ellipsoid. Although identified as a geometrical point for the purposes of illustration in the drawings, the term "focus" refers to a focal zone generally centered about an infinitisimally small focal point.

Although particular embodiments of the invention have been shown and described in full here, there is no intention to thereby limit the invention to the details of such embodiments. On the contrary, the intention is to cover all modifications, alternatives, embodiments, usages and equivalents of the subject invention as falling withing the spirit and scope of the invention, specification and the appended claims.

What is claimed is:

1. An illuminator and collector apparatus for fluorescence analysis wherein irradiation of a stream of particles by illuminating radiation stimulates detectable fluorescent radiation, comprising:
    a reflector having a concave reflector surface with a first focus and a second focus, said first focus being positioned in intersecting relationship with the stream of particles;
    illuminating means for impinging organized illuminating radiation upon said concave reflector surface so that the illuminating radiation is convergent upon said first focus after reflection from said concave reflector surface, whereby the particles are illuminated at the first focus from different directions by the illuminating radiation proceeding from said concave reflector surface;
    radiation separating means for separating the fluorescent radiation reflected off said concave reflector surface from the illuminating radiation directed toward said concave reflector surface, whereby the fluorescent radiation emanates from said first focus, reflects from said concave reflector surface so as to be focused on said second focus and is separated from the illuminating radiation for subsequent detection.

2. The illuminator and collector apparatus of claim 1, said concave reflector surface having a substantially ellipsoidal configuration.

3. The illuminator and collector apparatus of claim 2, said illuminating means including a source of illuminating radiation,
    said illuminating means further including means for providing divergent illuminating radiation to impinge upon said concave reflector surface.

4. The illuminator and collector apparatus of claim 1, said concave reflector surface having a substantially paraboloidal configuration and said second focus being positioned at infinity.

5. The illuminator and collector apparatus of claim 4, said illuminating means including a source of illuminating radiation,
    said illuminating means further including means for providing collimated illuminating radiation to impinge upon said concave reflector surface.

6. The illuminator and collector apparatus of claim 1, said concave reflector surface having a substantially hyperboloidal configuration and said second focus being a virtual focus.

7. The illuminator and collector apparatus of claim 6, said illuminating means including a source of illuminating radiation,
    said illuminating means further including means for providing convergent illuminating radiation to impinge upon said concave reflector surface.

8. The illuminator and collector apparatus of claim 1, said first focus and said second focus of said concave reflector surface defining an optical axis, said radiation separating means being positioned on said optical axis.

9. The illuminator and collector apparatus of claim 8 further comprising,
    a first orifice formed in a first barrier disposed in fluorescent light receiving relationship to said concave reflector surface.

10. The illuminator and collector apparatus of claim 9 further comprising,
    an optical detector disposed in fluorescent light receiving relationship to said radiation separating means, said first orifice positioned between said radiation separating means and said optical detector.

11. The illuminator and collector apparatus of claim 10 further comprising,
a second orifice positioned between said radiation separating means and said source of illuminating radiation.

12. The illuminator and collector apparatus of claim 9 further comprising,
means for varying the size of said first orifice.

13. The illuminator and collector apparatus of claim 8 further comprising,
a second orifice formed in a second barrier disposed to receive the illuminating radiation prior to the illuminating radiation reaching said concave reflector surface.

14. The illuminator and collector apparatus of claim 13,
said illuminating means including a source of illuminating radiation,
said second orifice being positioned between said radiation separating means and said source of illuminating radiation.

15. The illuminator and collector apparatus of claim 13 further comprising,
means for varying the size of said second orifice.

16. The illuminator and collector apparatus of claim 8 further comprising,
a first orifice formed in a first barrier disposed in a fluorescent light receiving relationship to said radiation separating means,
a second orifice formed in a second barrier disposed to receive the illuminating radiation prior to the illuminating radiation reaching said radiation separating means.

17. The illuminator and collector apparatus of claim 16 further comprising,
means for varying the sizes of said first and second orifices.

18. The illuminator and collector apparatus of claim 1 further comprising,
means for confining the organized illuminating radiation directed toward said concave reflector surface to a predetermined illumination solid angle formed with said first focus.

19. The illuminator and collector apparatus of claim 18 further comprising,
means for confining the fluorescent radiation reflected from said concave reflector surface to a collection solid angle formed with said first focus which is substantially equal to $4\pi$ steradians less said illumination solid angle.

20. The illuminator and collector apparatus of claim 1 further comprising,
means for confining the fluorescent radiation reflected from said concave reflector surface to a predetermined collection solid angle formed with said first focus.

21. The illuminator and collector apparatus of claim 1 further comprising,
means for separating the illuminating radiaion diverging from the first focus from the fluorescent radiation reflected from the concave reflector surface.

22. A method of illuminating a stream of particles to stimulate emission of fluorescent radiation, comprising the steps of:
illuminating the particles passing through a first focus of a concave reflector surface by reflecting organized illuminating radiation off of the concave reflector surface so that the illuminating radiation is convergent on the first focus,
separating the fluorescent radiation reflected off of the concave reflector surface from the illuminating radiation diverging from the first focus,
collecting the fluorescent radiation which has reflected from the concave reflector surface so as to be focused on a second focus of the concave reflector surface.

23. The method of claim 22,
the step of illuminating the particles comprising illuminating the particles over a predetermined illumination solid angle with respect to the first focus,
the step of collecting the fluorescent radiation comprising collecting the fluorescent light over a collection solid angle with respect to the first focus which is substantially equal to $4\pi$ steradians less the illumination solid angle.

24. The method of claim 23,
the step of collecting the fluorescent radiation further including adjusting the size of the fluorescent radiation reflected from the concave reflector surface.

25. The method of claim 23,
the step of illuminating the particles further including adjusting the size of the illuminating radiation directed toward the concave reflector surface.

26. The method of claim 25,
the step of collecting the fluorescent radiation further including adjusting the size of the fluorescent radiation reflected from the concave reflector surface.

27. The method of claim 22 further including the step of,
increasing the illumination solid angle while correspondingly decreasing the fluorescent collection solid angle until the desired illumination is obtained to provide reliable fluorescent signals.

* * * * *